United States Patent
Lenzi et al.

(10) Patent No.: US 10,799,373 B2
(45) Date of Patent: Oct. 13, 2020

(54) STANCE CONTROLLER AND RELATED METHODS

(71) Applicant: Rehabilitation Institute of Chicago, Chicago, IL (US)

(72) Inventors: Tommaso Lenzi, Chicago, IL (US); Jon Sensinger, Fredericton (CA)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 14/853,577

(22) Filed: Sep. 14, 2015

(65) Prior Publication Data

US 2016/0074180 A1     Mar. 17, 2016

Related U.S. Application Data

(63) Continuation-in-part of application No. 14/839,309, filed on Aug. 28, 2015, now Pat. No. 10,213,324.

(Continued)

(51) Int. Cl.

| | |
|---|---|
| *A61F 2/70* | (2006.01) |
| *A61F 2/64* | (2006.01) |
| *A61F 2/66* | (2006.01) |
| *A61F 2/68* | (2006.01) |
| *A61F 2/60* | (2006.01) |
| *A61F 2/76* | (2006.01) |
| *A61F 2/72* | (2006.01) |

(Continued)

(52) U.S. Cl.
CPC ............... *A61F 2/70* (2013.01); *A61F 2/60* (2013.01); *A61F 2/64* (2013.01); *A61F 2/6607* (2013.01); *A61F 2/68* (2013.01); *A61F 2/72* (2013.01); *A61F 2/80* (2013.01); *A61F 2002/701* (2013.01); *A61F 2002/704* (2013.01); *A61F 2002/74* (2013.01); *A61F 2002/762* (2013.01); *A61F 2002/764* (2013.01); *A61F 2002/7625* (2013.01); *A61F 2002/7635* (2013.01)

(58) Field of Classification Search
CPC .......................................................... A61F 2/70
See application file for complete search history.

(56) References Cited

U.S. PATENT DOCUMENTS

| | | | |
|---|---|---|---|
| 2006/0135883 A1* | 6/2006 | Jonsson | A61F 2/6607 600/546 |
| 2006/0249315 A1* | 11/2006 | Herr | A61F 2/60 180/8.1 |

(Continued)

OTHER PUBLICATIONS

Nordin M, Frankel V. Basic Biomechanics of the Musculoskeletal System. 4th edition. Lippencott Wiliams & Wilkins. 2012. Baltimore, MD. 226-232.*

(Continued)

*Primary Examiner* — Jacqueline Woznicki
(74) *Attorney, Agent, or Firm* — McAndrews, Held & Malloy, Ltd.

(57) ABSTRACT

Systems and methods are disclosed for operating a joint of a prosthesis during a phase of stance. In an embodiment, a method for such operation comprises determining a joint angle of the joint, determining a walking speed of the prosthesis, retrieving a torque value from a lookup table stored in a memory, on the basis of the joint angle and the walking speed, and initiating a signal to apply a torque to the joint of the prosthesis in an amount based on the torque value.

19 Claims, 7 Drawing Sheets

Related U.S. Application Data (60) Provisional application No. 62/049,686, filed on Sep. 12, 2014.

(51) Int. Cl.
*A61F 2/74* (2006.01)
*A61F 2/80* (2006.01)

(56) References Cited

U.S. PATENT DOCUMENTS

| | | | | |
|---|---|---|---|---|
| 2012/0259429 | A1* | 10/2012 | Han | A61F 5/0127 623/24 |
| 2012/0283844 | A1* | 11/2012 | Langlois | A61F 2/68 623/24 |
| 2015/0297364 | A1* | 10/2015 | Goldfarb | A61F 2/66 623/47 |

OTHER PUBLICATIONS

K. Ziegler-Graham, E. J. MacKenzie, P. L. Ephraim, T. G. Travison, and R. Brookmeyer, "Estimating the prevalence of limb loss in the United States: 2005 to 2050," Arch. Phys. Med. Rehab., vol. 89, No. 3, pp. 422-429, 2008.
R. L. Waters, J. Perry, D. Antonelli, and H. Hislop, "Energy cost of walking of amputees: The influence of level of amputation," J. Bone Joint Surg. Amer., vol. 58, No. 1, pp. 42-46, Jan. 1976.
M. Q. Liu, F. C. Anderson, M. H. Schwartz, and S. L. Delp, "Muscle contributions to support and progression over a range of walking speeds," J. Biomech., vol. 41, No. 15, pp. 3243-3252, Nov. 2008.
H. Sadeghi, P. Allard, and M. Duhaime, "Muscle power compensatory mechanisms in below-knee amputee gait," Amer. J. Phys. Med. Rehab., vol. 80, pp. 25-32, Jan. 2001.
R. Seroussi and A. Gitter, "Mechanical work adaptations of above-knee amputee ambulation," Arch. Phys. Med. Rehab., vol. 77, pp. 1209-1214, Nov. 1996. [6] H. M. Herr and A. M. Grabowski, "Bionic ankle-foot prosthesis normalizes walking gait for persons with leg amputation," Proc. Biol. Sci., vol. 279, No. 1728, pp. 457-464, Feb. 2012.
H. M. Herr and A. M. Grabowski, "Bionic ankle-foot prosthesis normalizes walking gait for persons with leg amputation," Proc. Biol. Sci., vol. 279, No. 1728, pp. 457-464, Feb. 2012.
S. K. Au, J. Weber, and H. Herr, "Powered ankle-foot prosthesis improves walking metabolic economy," IEEE Trans. Robot., vol. 25, No. 1, pp. 51-66, Feb. 2009.
P. Cherelle, V. Grosu, A. Matthys, B. Vanderborght, and D. Lefeber, "Design and validation of the ankle mimicking prosthetic foot 2.0.," IEEE Trans. Neural Syst. Rehab. Eng., vol. 22, No. 1, pp. 138-148, Oct. 2013.
L. Nolan, A. Wit, K. Dudzifiski, A. Lees, M. Lake, and M. Wychowañski, "Adjustments in gait symmetry with walking speed in trans-femoral and trans-tibial amputees," Gait Posture, vol. 17, No. 2, pp. 142-151, Apr. 2003.
D. A. Winter, "Energy generation and absorption at the ankle and knee during fast, natural, and slow cadences," Clin. Orthop. Relat. Res., vol. 175, pp. 147-154, May 1983.
J. M. Donelan, R. Kram, and A. D. Kuo, "Mechanical work for step-to-step transitions is a major determinant of the metabolic cost of human walking," J. Exp. Biol., vol. 205, pt. 23, pp. 3717-3127, Dec. 2002.
R. R. Neptune, S. A. Kautz, and F. E. Zajac, "Contributions of the individual ankle plantar flexors to support, forward progression and swing initiation during walking," J. Biomech., vol. 34, No. 11, pp. 1387-1398, Nov. 2001.
J. Doke, J. M. Donelan, and A. D. Kuo, "Mechanics and energetics of swinging the human leg," J. Exp. Biol., vol. 208, pt. 3, pp. 439-445, Feb. 2005.
F. Sup, A. Bohara, and M. Goldfarb, "Design and control of a powered transfemoral prosthesis," Int. J. Robot. Res., vol. 27, No. 2, pp. 263-273, Feb. 2008.

A. M. Simon, N. P. Fey, S. B. Finucane, R. D. Lipschutz, and L. J. Hargrove, "Strategies to reduce the configuration time for a powered knee and ankle prosthesis across multiple ambulation modes," in Proc. IEEE Int. Conf. Rehabilitation Robotics, Jun. 2013, pp. 1-6.
M. A. Holgate, W. B. Alexander, and T. G. Sugar, "Control algorithms for ankle robots: A reflection on the state-of-the-art and presentation of two novel algorithms," in Proc. BioRob 2nd IEEE RAS EMBS Int. Conf. Biomedical Robotics Biomechatronics, 2008, pp. 97-102.
R. D. Gregg and J. W. Sensinger, "Towards biomimetic virtual constraint control of a powered prosthetic leg," IEEE Trans. Control Syst. Technol., vol. 22, No. 1, pp. 246-254, Jan. 2014.
R. D. Gregg, T. Lenzi, L. J. Hargrove, and J. W. Sensinger, "Virtual constraint control of a powered prosthetic leg: From simulation to experiments with transfemoral amputees," IEEE Trans. Robot., to be published.
R. D. Gregg, T. Lenzi, N. P. Fey, L. J. Hargrove, and J. W. Sensinger, "Experimental effective shape control of a powered transfemoral prosthesis," in Proc. IEEE Int. Conf. Rehabilitation Robotics, Jun. 2013, pp. 1-7.
E. J. Rouse, R. D. Gregg, L. J. Hargrove, and J. W. Sensinger, "The difference between stiffness and quasistiffness in the context of biomechanical modeling," IEEE Trans. Biomed. Eng., vol. 60, No. 2, pp. 562-568, Feb. 2013.
R. Davis and P. DeLuca, "Gait characterization via dynamic joint stiffness," Gait Posture, vol. 4, No. 3, pp. 224-231, 1996.
D. A. Winter, Biomechanics and Motor Control of Human Movement, 4th ed. New York: Wiley, 2009 p. 383.
K. Shamaei, G. S. Sawicki, and A. M. Dollar, "Estimation of quasistiffness of the human knee in the stance phase of walking," PLoS One, vol. 8, No. 3, p. e59993, Jan. 2013.
K. Shamaei, G. S. Sawicki, and A. M. Dollar, "Estimation of quasistiffness and propulsive work of the human ankle in the stance phase of walking," PLoS One, vol. 8, No. 3, p. e59935, Jan. 2013.
D. A. Winter and D. G. E. Robertson, "Joint torque and energy patterns in normal gait," Biol. Cybern., vol. 29, No. 3, pp. 137-142, 1978.
S. Au and H. Herr, "Powered ankle-foot prosthesis," IEEE Robot. Automat. Mag., vol. 15, No. 3, pp. 52-59, Sep. 2008.
H. Vallery, J. Veneman, E. van Asseldonk, R. Ekkelenkamp, M. Buss, and H. van Der Kooij, "Compliant actuation of rehabilitation robots," IEEE Robot. Automat. Mag., vol. 15, No. 3, pp. 60-69, Sep. 2008.
F. Sup, H. A. Varol, J. Mitchell, T. J. Withrow, and M. Goldfarb, "Selfcontained powered knee and ankle prosthesis: Initial evaluation on a transfemoral amputee," in Proc. IEEE Int. Conf. Rehabilitation Robotics, Jun. 2009, pp. 638-644.
R. Mahony, S. Member, T. Hamel, and J. Pflimlin, "Nonlinear complementary filters on the special orthogonal group," IEEE Trans. Autom. Control, vol. 53, No. 5, pp. 1203-1218, 2008.
S. Yang and Q. Li, "Inertial sensor-based methods in walking speed estimation: A systematic review," Sensors, vol. 12, No. 5, pp. 6102-6116, Jan. 2012.
R. R. Torrealba, J. Cappelletto, L. Fermín-León, J. C. Grieco, and G. Ferná ndez-López, "Statistics-based technique for automated detection of gait events from accelerometer signals," Electron. Lett., vol. 46, No. 22, p. 1483, 2010.
M. A. Holgate, T. G. Sugar, and W. B. Alexander, "A novel control algorithm for wearable robotics using phase plane invariants," in Proc. IEEE Int. Conf. Robotics Automation, 2009, pp. 3845-3850.
T. Lenzi, M. C. Carrozza, and S. K. Agrawal, "Powered hip exoskeletons can reduce the user's hip and ankle muscle activations during walking," IEEE Trans. Neural Syst. Rehab. Eng., vol. 21, No. 6, pp. 938-948, Nov. 2013.
A. H. Hansen, D. S. Childress, S. C. Miff, S. A. Gard, and K. P. Mesplay, "The human ankle during walking: Implications for design of biomimetic ankle prostheses," J. Biomech., vol. 37, No. 10, pp. 1467-1474, 2004.
M. L. Palmer, "Sagittal plane characterization of normal human ankle function across a range of walking speeds," M.S. thesis Mech. Eng., Massachusetts Inst. Technology, Cambridge, MA, 2002.
A. M. Simon, K. A. Ingraham, N. P. Fey, S. B. Finucane, R. D. Lipschutz, A. J. Young, and L. J. Hargrove, "Configuring a powered (56) References Cited

OTHER PUBLICATIONS knee and ankle prosthesis for transfemoral amputees within five specific ambulation modes," PLoS One, vol. 9, No. 6, p. e99387, Jan. 2014.
R. Seroussi and A. Gitter, "Mechanical work adaptations of above-knee amputee ambulation," Arch. Phys. Med. Rehab., vol. 77, No. 11, pp. 1209-1214, Nov. 1996.
S. H. Collins and A. D. Kuo, "Recycling energy to restore impaired ankle function during human walking," PLoS One, vol. 5, No. 2, p. e9307, Jan. 2010.
J. L. Johansson, D. M. Sherrill, P. O. Riley, P. Bonato, and H. Herr, "A clinical comparison of variable-damping and mechanically passive prosthetic knee devices," Amer. J. Phys. Med. Rehab., vol. 84, No. 8, pp. 563-575, Aug. 2005.
R. J. Zmitrewicz, R. R. Neptune, and K. Sasaki, "Mechanical energetic contributions from individual muscles and elastic prosthetic feet during symmetric unilateral transtibial amputee walking: A theoretical study," J. Biomech., vol. 10, No. 8, pp. 1824-1831, Jan. 2007.
Pell et al., Quality of Life Following Lower Limb Amputation for Peripheral Arterial Disease, Eur. J. Vasc. Surg., Jul. 1993, vol. 7, pp. 448-451.
Hitt et al., An Active Foot-Ankle Prosthesis with Biomechanical Energy Regeneration, J. Med. Devices, Mar. 2010, vol. 4, 011003-1-011003-9.

\* cited by examiner

STANCE CONTROLLER AND RELATED METHODS

CROSS REFERENCE TO RELATED APPLICATIONS

This application is a continuation-in-part to U.S. patent application Ser. No. 14/839,309 by Lenzi et al, Minimum Jerk Swing Control for Assistive Device, filed Aug. 28, 2015, which is incorporated by reference. This application claims benefit to U.S. Provisional Patent Application 62/049,686, filed on Sep. 12, 2014, which is incorporated by reference.

STATEMENT REGARDING FEDERALLY SPONSORED RESEARCH OR DEVELOPMENT

This invention was made with government support under award W81XWH-09-2-0020 awarded by the United States Army. The government has certain rights in the invention.

BACKGROUND

Every year, 185,000 people undergo a major lower-limb amputation in the United States. Functional impairment following loss of a leg is particularly severe for persons with transfemoral amputations, who expend up to twice the metabolic effort to walk at half the speed of able-bodied persons, and experience a higher risk of falls and incidence of secondary conditions such as back pain, depression, and osteoarthritis.

Experimental studies and gait simulations show that passive prostheses cannot fully replace the biomechanical function of intact legs, as they are unable to provide biologically-accurate torque at the joint level. Persons with amputations must compensate for this deficiency by increased effort of both the residual limb and contralateral leg. However, these compensatory strategies result in kinetic and kinematics gait asymmetries that reduce gait efficiency and cause higher stress on the musculoskeletal apparatus.

Thanks to recent improvements on motor, battery, and microcontroller technologies, robotic prostheses have become a reality. Robotic prostheses can actively regulate joint torque and release positive net-energy during the gait cycle. Thus they can closely match the kinetics and kinematics of an intact leg during walking, possibly restoring physiological gait efficiency and stability.

Despite promising results obtained so far, several challenges remain in the design and control of a robotic prosthesis. From a control perspective, one of the main challenges is to provide biologically accurate torque across a wide range of walking speeds, without requiring speed-specific prosthesis tuning, which is unfeasible in clinical practice. Joint torque demand is not fixed but depends on walking speed. In stance phase (i.e., foot on the ground), torque profiles change non-linearly with walking speed to properly support body weight against gravity, and to propel the body mass in a forward direction. In swing phase (i.e., foot off the ground), a progressively faster movement must be generated at increased walking speeds to ensure timely placement of the foot in preparation for the subsequent heel-strike, regardless of the initial swing conditions generated by the stance controller. Similarly, able-bodied persons modulate the activation of their lower-limb muscle to adapt the leg joint torque based on level ground-inclination.

Available transfemoral prosthesis controllers cannot adapt to different walking speeds or ground inclinations. Impedance-inspired control defines the joint torque as a parametric function of joint angle and velocity, with different stiffness, damping, and equilibrium values for each discrete phase of the gait cycle. To obtain biologically-accurate torques, impedance-inspired control requires explicit tuning of all parameters through experiments performed at a specific walking speed. At speeds other than that specific speed or ground inclinations, prosthesis function is not optimal; it provides incorrect body support and propulsion during stance phase and incorrect movement trajectory and duration in swing phase. Most importantly, because of speed-dependent parameters, impedance-inspired control requires user-specific tuning. Different persons use different gait cadences—and therefore different joint velocities—to walk at the same speed.

Other control approaches have been described in H. M. Hen and A. M. Grabowski, "Bionic ankle-foot prosthesis normalizes walking gait for persons with leg amputation.," Proc. Biol. Sci., vol. 279, no. 1728, pp. 457-64, February 2012, and M. A. Holgate, W. B. Alexander, and T. G. Sugar, "Control Algorithms for Ankle Robots: A Reflection on the State-of-the-Art and Presentation of Two Novel Algorithms," pp. 97-102, 2008.

Other control approaches have also been described in J. K. Hitt, T. G. Sugar, M. Holgate, and R. Bellman, "An Active Foot-Ankle Prosthesis With Biomechanical Energy Regeneration," J. Med. Device., vol. 4, no. 1, p. 011003, 2010; M. A. Holgate, W. B. Alexander, and T. G. Sugar, "Control Algorithms for Ankle Robots: A Reflection on the State-of-the-Art and Presentation of Two Novel Algorithms," pp. 97-102, 2008; T. Lenzi, M. C. Carrozza, and S. Agrawal, "Powered Hip Exoskeletons Can Reduce the User's Hip and Ankle Muscle Activations During Walking.," IEEE Trans. Neural Syst. Rehabil. Eng., no. c, pp. 1-1, March 2013.

BRIEF SUMMARY

We have prepared a new control framework that allows robotic transfemoral prostheses to generate biologically accurate kinetics and kinematics without the need for tuning specific to walking speed, cadence, or ground inclination. Based on the adaptation of intact leg biomechanics to different walking speeds and ground inclination, our control framework, in an embodiment, enforces quasi-stiffness profiles in the stance phase of gait.

DETAILED DESCRIPTION

The ankle torque-angle relationship has typically been studied during performance of a specific task such as walking or running. In these cases, the derivative of the torque-angle relationship with respect to angle is known as the quasi-stiffness. In other words, the quasi-stiffness is the derivative of the torque-angle relationship during the execution of a dynamic task (for example walking, running, or jumping). Quasi-stiffness profiles change consistently as a function of walking speed, resulting in speed specific torque-angle curves during stance phase.

Direct encoding of intact leg quasi-stiffness profiles in the stance controller circumvents the need for explicit tuning of stance phase control parameters. Moreover, biologically accurate torques for any walking speed and ground inclination can result from the interpolation of a few speed and ground inclination specific quasi-stiffness profiles—obtained from intact leg studies—based on the walking speed measured by the prosthesis.

In an embodiment, during swing, a controller may employ a minimum jerk trajectory generator that can produce biologically accurate swing movements, across different walking speeds and users, independently of stance control. In an embodiment, the minimum-jerk trajectory generator can take whatever joint angle and velocity at the stance/swing phase transition, and drive the prosthesis on a physiological trajectory in the desired amount of time. Physiological stance and swing phase timing across different walking speeds can then be obtained by imposing swing movement duration proportional to stance phase duration. Moreover, the controller may regulate the maximum knee flexion angle independently of swing phase duration to help ensure adequate foot clearance.

As a preliminary evaluation, we implemented the controller on the second generation of the Vanderbilt transfemoral prosthesis. An example of this prosthesis is shown in FIG. 1, being worn by an able-bodied user using a bypass adapter. The user walked on a treadmill at five different walking speeds while we recorded prosthesis kinetics and kinematics to assess controller function. Experimental results showed that our controller successfully adapted the prosthesis action according to walking speed.

Figure 1A:
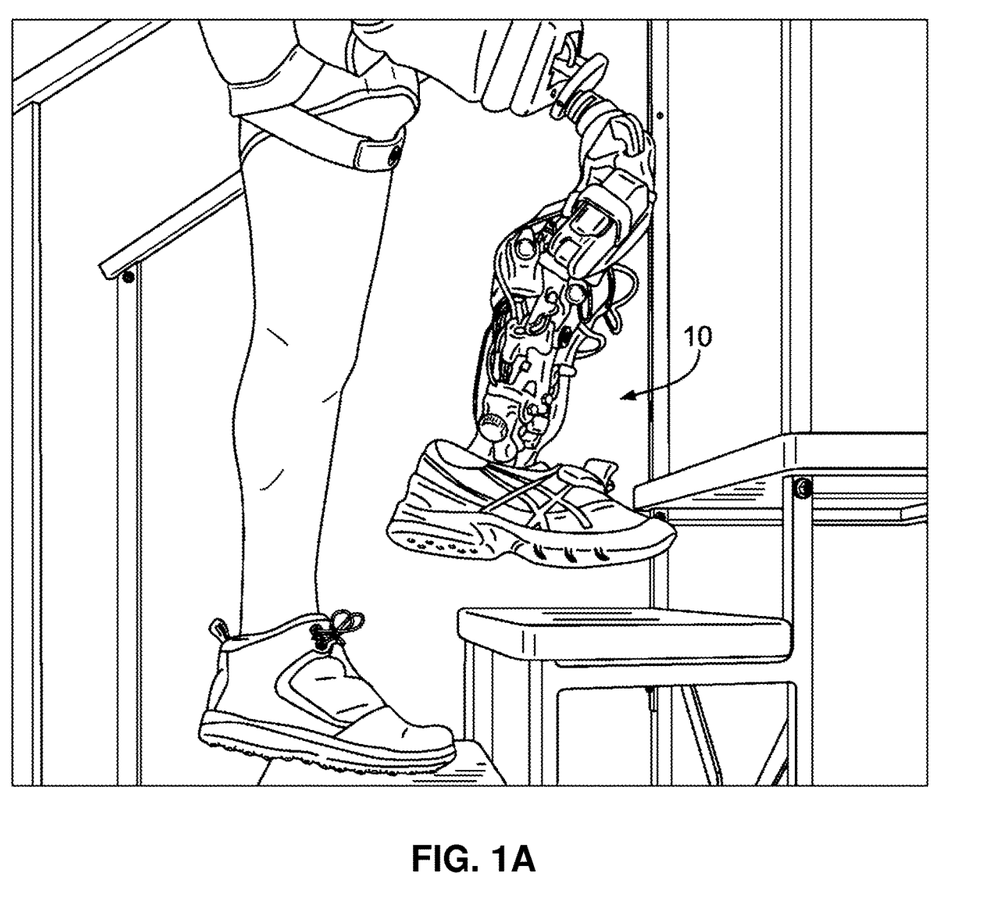
FIG. 1A displays a side view of an embodiment of a prosthesis.
Figure 1B:
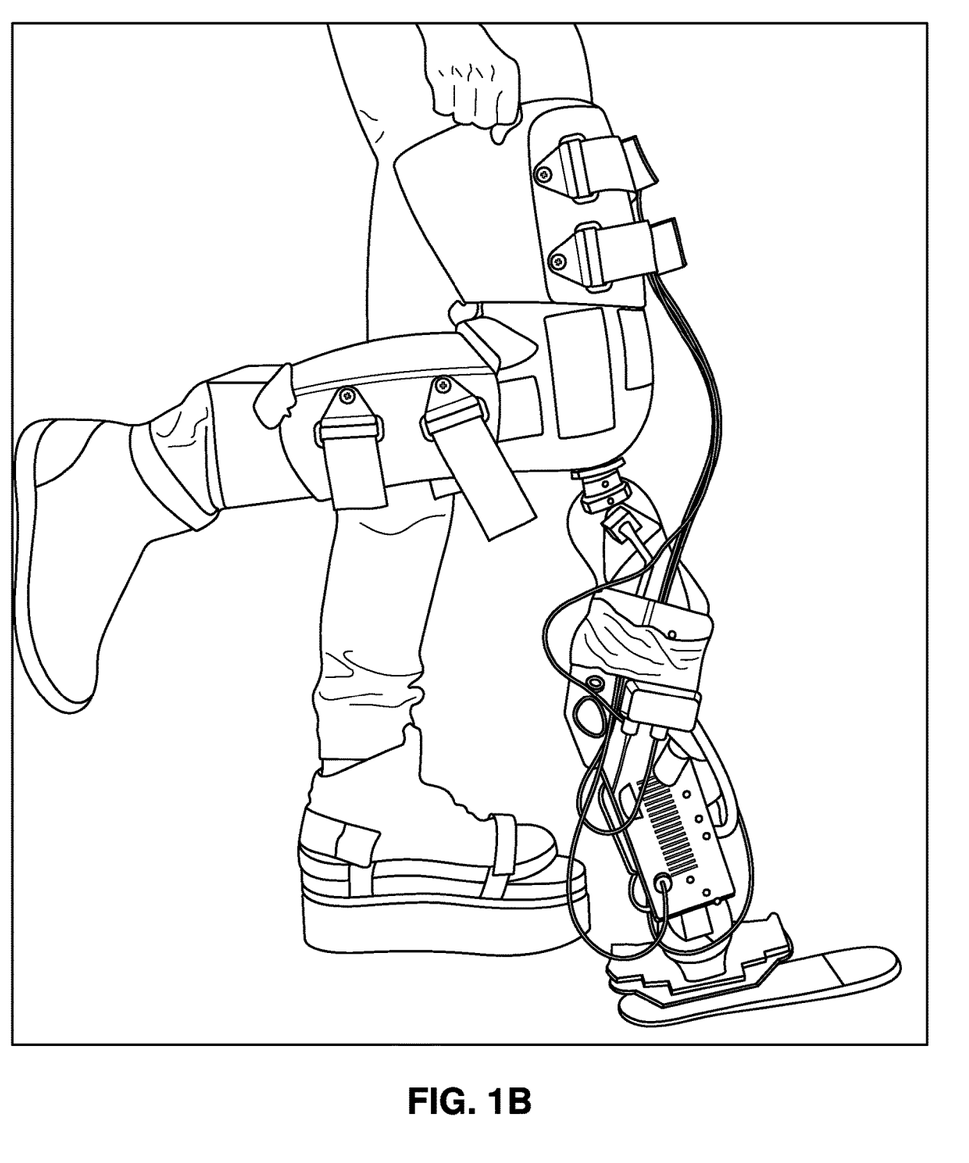
FIG. 1B displays an embodiment of a transfemoral prosthesis being worn by an able-bodied user using a bypass adapter.
Figure 1C:
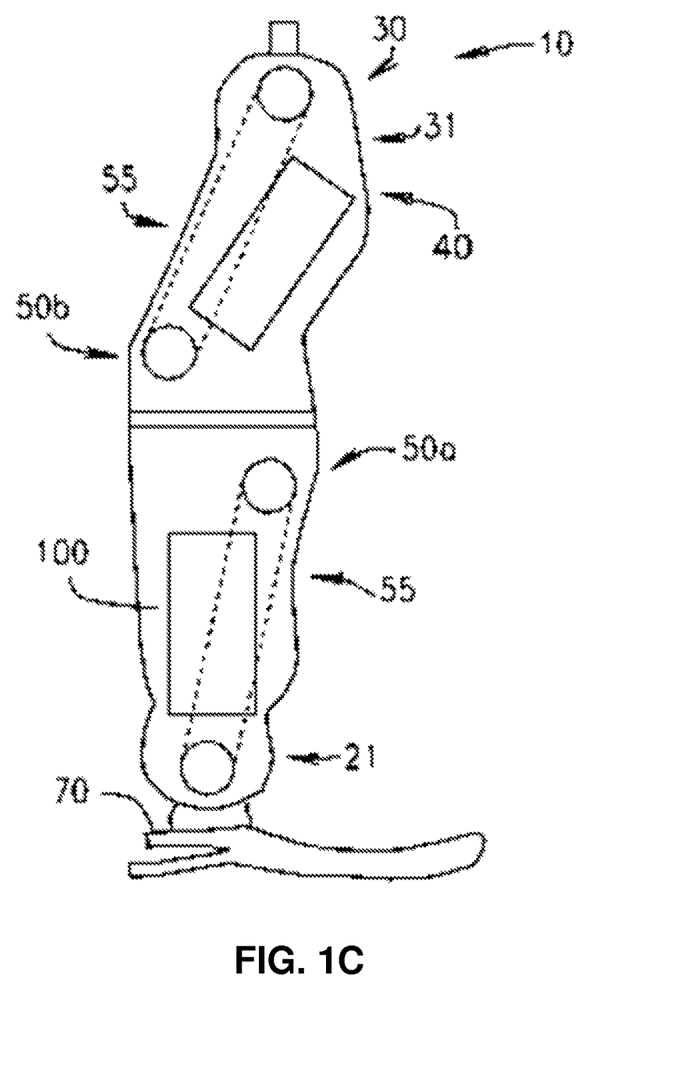
FIG. 1C displays a representation of an embodiment of a prosthesis.

Prosthesis 10 is shown in FIGS. 1A, 1B, and 1C. Prosthesis 10 may comprise a powered knee, a powered ankle, and a powered shank. The knee and the ankle are each coupled to one or more motors and one or more transmissions that together are capable of producing physiological levels of torque. The motors may be brushless DC motors to deliver biomechanically appropriate torque and power at the knee and ankle joints. Prosthesis 10 and its related powered components are powered by a battery. Although prosthesis 10 is disclosed as an embodiment, other assistive devices, such as orthoses and exoskeletons, may incorporate a control module using the methods described here, including but not limited to the prosthesis described in U.S. Provisional Patent Application No. 62/088,849 to Kuiken et al, titled Powered and Passive Assistive Device and Related Methods, filed Dec. 8, 2014, which is incorporated by reference.

Prosthesis 10 further comprises mechanical sensors. In one embodiment, mechanical sensors include a load cell that measures the vertical load along the long axis of prosthesis 10; a position sensor and a velocity sensor that measure the position and velocity of the knee; a position sensor and a velocity sensor that measure the position and velocity of ankle; and a six degree of freedom inertial measurement unit (IMU) at the shank, comprising accelerometers and gyroscopes for measuring accelerations and angular velocities. Mechanical sensors may be contained within the assembly of prosthesis 10, attached to prosthesis 10, or attached to the user of prosthesis 10. In other embodiments, the knee and ankle could be powered instead with hydraulics, compressed gas, or other mechanisms.

FIG. 1C displays another view of the prosthesis 10 that may be operated according to the systems and methods described herein. Prosthesis 10 may comprise a powered ankle 21 and a powered knee 31. Each of the ankle 20 and knee 30 (each known herein as a "joint") may be coupled to an encoder 40 that can measure the joint's angle and velocity. Each joint may also be coupled to a motor 50 and transmission 55 that together are capable of producing physiological levels of torque. 50a indicates the motor coupled to the ankle and 50b indicates the motor coupled to the knee. Prosthesis 10 and its related components may be the prosthetic limb with powered knee and ankle joints developed by the Vanderbilt Center for Intelligent Mechatronics (Vanderbilt University, TN) and commercialized by Freedom Innovations (Irvine, Calif.) or another powered prosthetic limb. Prosthesis 10 and its components may be powered by a battery 40.

A socket may be used in conjunction with the prosthesis 10. The socket fits onto the residual limb of a user. The socket may comprise a lining and an exterior shell. The prosthesis 10 may be coupled to the socket by a pyramid style connector or other appropriate connector. The socket may be coupled to electrodes. In one embodiment, the electrodes are embedded in the socket and contact the user's skin. The electrodes measure EMG signals from the user's residual limb muscles when the user operates the prosthesis 10. In one embodiment, the electrodes may be placed on the following muscles of the user: semitendinosus, biceps femoris, tensor fasciae latae, rectus femoris, vastus lateralis, vastus medialis, sartorius, adductor magnus, and gracilis.

Figure 6:
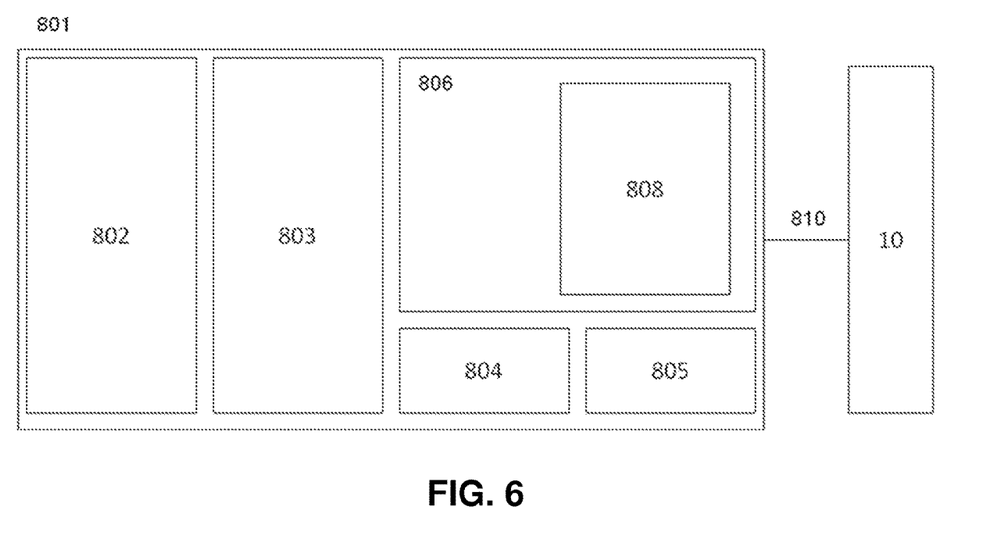
FIG. 6 displays a representation of an embodiment of a controller used to control a prosthesis.

In one embodiment, a controller is physically attached to the socket or other part, such as to the prosthesis 10, and connected to the components of the prosthesis 10 and to electrodes by a communication bus. As shown in FIG. 6, the controller may comprise a controller board 801, which may comprise a microprocessor 802, memory 803, signal filtering hardware 804, and sampling hardware 805. A control module 806 may be programmed onto the controller board 801 and may be executed by the controller board 801, such as by the controller board's microprocessor 802. The control module 806 may comprise a stance phase control module 808. The controller board 801 may communicate with the prosthesis by a bus 810. For instance, the controller board 801 may use the bus 810 to send a signal to provide a torque to a joint of the prosthesis 10, such as the knee joint or the ankle joint.

An embedded control system may execute a closed-loop torque control modules for the ankle and knee joints. In one embodiment, a remote computer using a hard real-time operative system (xPC target, Mathworks, USA) runs the algorithms for the estimate of gait phase and walking speed, as well as the stance phase and swing phase control modules. Communication between the embedded and remote systems is handled by a high-speed CAN bus (CAN-AC2-PCI, Softing, USA). Communication, processing, and data recording run on the remote control system at the fixed sampling rate of 1 KHz. In another embodiment, the operations of the modules that reside the remote controller shown in FIG. 2 instead may be incorporated into hardware controllers or other control modules attached to the prosthesis 10, such as the controller board 801.

We next present the overall prosthesis control architecture and its implementation on the a prosthesis 10. We then describe the protocol for the experimental characterization and data analysis.

Controller Design

Figure 2:
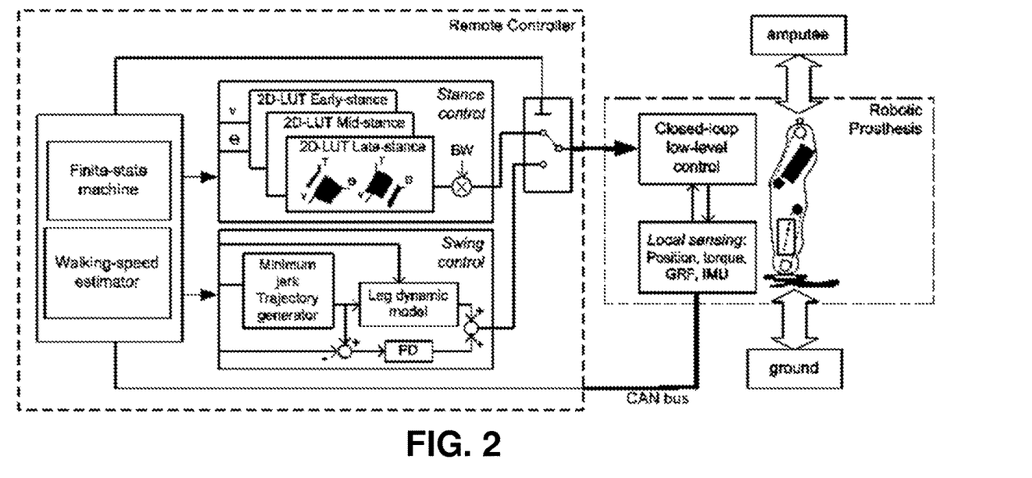
FIG. 2 displays a block-diagram representation of the controller described herein.

A block-diagram representation of the control module programmed in the controller is shown at FIG. 2. The control module programmed in the controller can comprise three stages: (1) identification of gait-phase, walking speed/cadence, and ground inclination; (2) planning of prosthesis joint torques; (3) attainment of desired torque at the prosthetic joints. As shown in FIG. 2, a control module in a remote controller receives the local sensing information from the leg through a CAN bus. The information is first processed by a finite-state machine and walking speed estimator that identifies the current phase of the gait-cycle as well as the walking speed. Based on these estimates, a specific control module is selected. In stance phase, a specific bi-dimensional look-up table (2D-LUT) contained the quasi-stiffness profile for each sub-phase of stance and each joint. Through interpolation, the 2D-LUTs compute the reference torques for any specific angular position and walking speed. Other embodiments may include control of swing phase as well as stance phase. In swing phase, in another embodiment, a biomimetic minimum-jerk angular trajectory may be generated and imposed using a combination of feed-forward and feedback position control. Finally, the controller may initiate a signal to apply a torque to the joint of the prosthesis in an amount based on the torque value. For example, a reference torque may be transmitted to the low-level control module embedded in the Vanderbilt leg control system or otherwise may be initiated to prosthesis 10.

In an embodiment, the walking speed estimate relies on a two-step approach. First, it estimates the prosthesis shank orientation in the sagittal plane using a complementary filter to fuse the data from an accelerometer and a gyroscope on the prosthesis. A complementary filter is described, for example, in Higgins, Walter T. "A comparison of complementary and Kalman filtering." IEEE Transactions on Aerospace and Electronic Systems 11.3 (1975): 321-325, incorporated by reference. A three-segment planar model of the user's leg is then used to compute the hip-forward velocity in the sagittal plane and the resulting walking speed. The error of the walking speed estimate has been determined experimentally to be 8%, in agreement with previous studies.

In an embodiment, the ground inclination estimate is obtained by measuring the foot orientation in the sagittal plane when the foot speed is below a specific threshold—for example 10 deg/s—for a defined amount of time—for example 50 ms. Within each gait cycle, the foot is stationary on the ground for a given period of time during the stance phase. This specific lapse of time within the stance phase is sometimes called "foot flat" in the biomechanics literature. During this period of time the orientation of the foot is stationary, and corresponds to the orientation of the ground. Therefore, by measuring the orientation of the foot when it is flat on the ground, the controller may determine a measurement of the orientation of the ground.

The foot orientation in the sagittal plane can be estimated as the sum of the shank orientation (obtained as described in the above paragraph) and the ankle angle position measured for example by the prosthesis ankle joint encoder. Alternatively, the foot orientation can be estimated by using a complementary filter to optimally fuse the data from an accelerometer and a gyroscope located on the prosthesis foot.

Gait phase identification relies on a finite-state machine. As for previously proposed controllers, our controller uses a finite-state machine. The finite-state machine may combine output from angular position, inertial measurement unit (IMU), and ground reaction force (GRF) sensors on the prosthesis to estimate whether the user is standing or walking. For instance, when the sensors indicate that the load is greater than 5% of the user's body weight and the speed of the shank is less than 10 degrees/second, the controller determines the user is standing. During walking, the finite-state machine divides the gait cycle into four phases: early stance, mid-stance, late stance, and swing phase. Each phase may then be controlled in a different way.

The stance control module may be used for the phases of stance, such as for early stance, mid-stance, and late stance. The stance phase control module 808 may define the desired torque-angle profiles for each of the ankle and knee joints based on the gait phase and walking speed estimates of the prosthesis 10. For each joint and for each phase of stance, we encoded the intact-leg quasi stiffness profiles extracted from able-bodied data found at D. A. Winter, Biomechanics and Motor Control of Human Movement, vol. 2nd. 1990 (incorporated by reference), p. 277 at two different walking speeds—0.5 m/s and 1.5 m/s—on a bi-dimensional lookup table (2D-LUT). The walking data used in our controller is from the Winter reference and the relevant portions are included at the appendix of this patent application.

Each 2D-LUT takes the current joint angle and walking speed estimate as inputs and outputs the desired torque, normalized by the body weight of the user. A torque-angle curve specific for any walking speed is then obtained through interpolation. Saturation occurs for input values outside the 2D-LUT boundaries. The output of each 2D-LUT is multiplied by the user's body weight to define the set-point torque for the closed-loop low-level control. Finally, a low-pass filter is used to smooth the desired torque output during the 20 ms following any transition between different 2D-LUTs.

Alternatively, for each stance phase, the stance control module may determine the desired torque-angle profiles for the ankle and knee joints based on the joint's current angle, the walking speed, and the ground inclination. In this embodiment, for each joint and for each phase of gait, the controller may store encoded intact-leg quasi stiffness profiles that have been extracted from able-bodied data in a tri-dimensional lookup table (3D-LUT). Such data may be found, for example, in Bovi, Gabriele, et al. "A multiple-task gait analysis approach: kinematic, kinetic and EMG reference data for healthy young and adult subjects." Gait & posture 33.1 (2011): 6-13, and McIntosh, Andrew Stuart, et al. "Gait dynamics on an inclined walkway." Journal of biomechanics 39.13 (2006): 2491-2502, each of which is incorporated by reference. While the prosthesis 10 is in operation, the controller provides the ankle 3D-LUT with the current ankle angle, walking speed, and ground orientation estimate as inputs, and outputs the desired torque, normalized by the body weight of the user. Similarly, while the prosthesis 10 is in operation, the controller provides the knee 3D-LUT with the current knee angle, walking speed, and ground orientation estimate as inputs, and output the desired torque, normalized by the user's body weight. In this way, the controller is able to obtain through interpolation a torque-angle curve specific for any walking speed and ground inclination. Saturation may occur for input values outside the 3D-LUT boundaries. To normalize the output by body weight, the output of each 3D-LUT may be multiplied by the user's body weight to define the set-point torque for the closed-loop low-level control. Finally, a low-pass filter may be used to smooth the desired torque output during the 20 ms following any transition between different 3D-LUTs.

In an embodiment, the controller transitions between early stance, mid-stance, and late stance phases. For instance, our controller transitioned to early stance when the sensors indicate that the load on the prosthesis 10 is greater than 5% of the user's body weight and the prior state was swing, to mid-stance when movement of the ankle inverts from plantarflexion to dorsiflexion (as determined by the sensors) and the prior stance was early stance, and to late stance when the movement of the ankle inverts from dorsiflexion to plantarflexion (as determined by the sensors) and the prior state was mid-stance. It should be understood that there are other ways to set the controller to a particular phase, and that stance may be divided differently than as described here. Inversion of the ankle may be determined by detecting a change in ankle angle velocity from a velocity sensor, from a negative value to a positive value (from plantarflexion to dorsiflexion) or from a positive value to a negative value (from dorsiflexion to plantarflexion). If the user stops moving while the controller is in a stance phase, the controller sets the mode of the prosthesis to standing. One result of embodiments of the controller is that when the prosthesis is standing, the ankle behaves as a constant spring while the knee behaves as a constant damper, emulating the behavior of a commercially-available passive prosthesis.

As described in more detail in U.S. patent application Ser. No. 14/839,309 by Lenzi et al, Minimum Jerk Swing Control for Assistive Device, filed Aug. 28, 2015, incorporated by reference, in swing phase, the prosthesis controller uses an open-loop position control based on a minimum jerk principle. As the finite-state machine enters into swing mode (i.e., foot off the ground), the swing phase controller computes the coefficients of a 5th order polynomial function that generates the desired minimum-jerk position trajectory. The duration of the swing movement is set to be 0.30 and 0.60 times the previous stance duration for the ankle and knee joints, respectively, based on intact leg biomechanics in D. A. Winter, Biomechanics and Motor Control of Human Movement, vol. 2nd. 1990. The initial joint angle and velocity of the minimum-jerk trajectory equal their respective measured values at the stance/swing phase transition. The final angle, velocity, and acceleration are set to zero for both the ankle and knee joints. A unique minimum-jerk trajectory is used for the ankle joint, whereas the knee trajectory comprises two parts. The first part starts with the knee angle and velocity measured at the stance/swing phase transition and ends at the point of maximum knee flexion with zero velocity. The second part starts from the maximum knee flexion and ends with the knee fully extended with zero velocity and acceleration. The acceleration at maximum knee flexion as well as the initial acceleration of the ankle joint was optimized based on able-bodied data. The maximum knee flexion angle is regulated based on the user's anthropometric data to ensure appropriate foot clearance, despite the fixed size of the prosthesis shank. A strong feed-forward torque command and a weaker feedback position control with proportional and derivative terms enforce the desired angular trajectory of the prosthesis. While the feed-forward command accounts for the inertial, gravitational, and frictional components, the feedback loop reacts to contingent disturbances occurring during the swing movement and compensates for possible inaccuracy in the leg dynamic model. The torque references computed by the stance and swing controller are then imposed through low-level closed-loop control.

Figure 7:
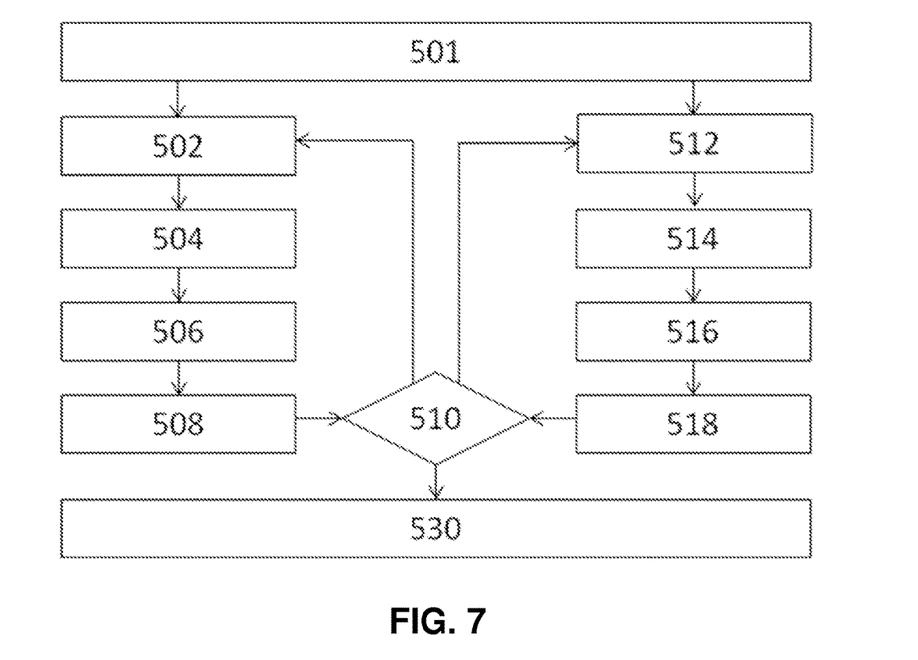
FIG. 7 displays a block representation of a method of operating a prosthesis.

FIG. 7 displays a flow chart that outlines certain methods of the embodiments described above for a prosthesis operating from a stance phase to a next phase. For instance, in an embodiment, if the stance phase is initial stance, the next phase is mid-stance; if the stance phase is mid-stance, then the next phase is late stance; if the stance phase is late stance, then the next phase is swing.

In 501, the prosthesis is in the stance phase. In 502, the controller may determine the angle of the knee joint of the prosthesis, using the methods described above or using other known methods. In 504, the controller may determine the walking speed of the prosthesis, using the methods described above or other known methods.

In 506, the controller may retrieve a torque value from a lookup table stored in a memory. For example, if the stance phase is early stance, then the lookup table that will be used is one associated with early stance. If the stance phase is mid-stance, then the lookup table that will be used is one associated with mid-stance. If the stance phase is late stance, then the lookup table that will be used is one associated with late stance. In an embodiment, in 506 the torque value may be retrieved at least on the basis of the knee angle and the walking speed. In another embodiment, the torque angle may be retrieved at least on the basis of the knee angle, the walking speed, and the ground inclination. In an embodiment, if a value does not exist in the lookup table, the value may be determined by interpolation, such as by interpolation of adjacent values in the lookup table.

In 508, the controller may initiate a signal to apply a torque to the knee joint of the prosthesis, in an amount based on the torque value retrieved from the lookup table. In an embodiment, the amount may be based on the torque value and normalized on the basis of the weight of the user of the prosthesis. In 510, the controller checks whether the prosthesis 10 has entered the next phase. If the prosthesis has not entered the next phase, the controller returns to 502. In this way the controller is continuously adjusting the torque value to the knee joint while the prosthesis 10 is in the stance phase.

Moreover, the controller may perform similar steps for the ankle joint during an initial stance phase. In 512, the controller may determine the angle of the ankle joint of the prosthesis. In 514, the controller may determine the walking speed of the prosthesis. In 516, the controller may retrieve a torque value from a lookup table stored in a memory. In an embodiment, the torque value may be retrieved at least on the basis of the ankle angle and the walking speed. In another embodiment, the torque angle may be retrieved at least on the basis of the ankle angle, the walking speed, and the ground inclination. In an embodiment, if a value does not exist in the lookup table, the value may be determined by interpolation, such as by interpolation of adjacent values in the lookup table. In 518, the controller may initiate a signal to apply a torque to the ankle joint of the prosthesis, in an amount based on the torque value retrieved from the lookup table. In an embodiment, the amount may be based on the torque value and normalized on the basis of the weight of the user of the prosthesis. In 510, the controller checks whether the prosthesis 10 has entered the next phase. If not, the controller returns to 512. In this way the controller is continuously adjusting the torque value to the ankle joint while the prosthesis 10 is in the stance phase. It should be apparent to one of ordinary skill in the art that the steps 502, 504, 506, and 508 may be taken concurrently, before, or after the steps 512, 514, 516, and 518, that not all the steps are essential to the operation of the prosthesis, and that other steps could be performed in between the steps shown in FIG. 7.

Implementation on the Vanderbilt Leg

The proposed control framework has been implemented on a self-contained ankle and knee prosthesis, previously developed at Vanderbilt University. The prosthesis can produce biologically-appropriate torque, power, and range-of-motion at the ankle and knee joints. This prosthesis is battery operated and uses a brushless DC motor controlled by custom servo amplifiers. The embedded control system of the prosthesis runs the closed-loop torque controllers for the ankle and knee joints. A remote computer using a hard real-time operative system (xPC target, Mathworks, USA) runs the algorithms to estimate gait-phase and walking speed, as well as the stance-phase and swing-phase controllers. Communications between the embedded and the remote systems are handled by a high-speed CAN bus (CAN-AC2-PCI, Softing, USA). An embedded controller transmits the local sensing information to the remote system, which processes this information, computes the reference values, and sends them back to the embedded closed-loop controllers. The remote system also saves all measured and processed variables. Communication, processing, and data recording run on the remote control system at a fixed sampling rate of 1 KHz.

Experimental Procedure and Data Analysis

An able-bodied user was fitted with a bypass adapter that constrained the thigh and shank, locking the knee at 90° of flexion (see FIG. 1). A custom foot lift on the contralateral leg compensated for the increased height on the prosthesis side caused by the bypass adapter. The user walked with the robotic prosthesis attached to the right (dominant) leg on a treadmill at five different constant walking speeds: 1.40, 1.70, 2.0, 2.3, and 2.6 mph (i.e., 0.62, 0.76, 0.89, 1.02, and 1.16 m/s). Each walking session lasted 2 minutes, and the user rested for 5 minutes between sessions.

Prosthesis GRF, torque, angle, and velocity profiles were recorded from local sensors on the prosthesis. Joint power was obtained during post-processing. To attenuate sensor noise for proper data analysis, we filtered all data using a low-pass back and forth first-order Butterworth filter with a cutoff frequency of 10 Hz. Joint torque, power, and work were normalized by dividing by the user's body weight. For each walking speed, we separated raw data into strides (i.e., the time interval between two consecutive heel-strike events on the prosthesis side) using the output of the GRF sensor on the prosthesis. Within each stride, we computed (i) the maximum and minimum angles for knee and ankle joints; (ii) the duration of stance phase, swing phase, and gait cycle; and (iii) the mean walking speed. In addition, we computed the joint mechanical work for each sub-phase of stance and overall stance phase duration by integrating the torque angle curve. The first and final three strides from each walking session were omitted from the analysis to avoid including non-steady state walking. Finally, we computed the angle, torque, and power profiles of the ankle and knee joint averaged over all the steady-state strides recorded at each constant walking speed. All data processing was performed using MATLAB (MathWorks, Natick, Mass., USA).

Results and Discussion

Figure 3:
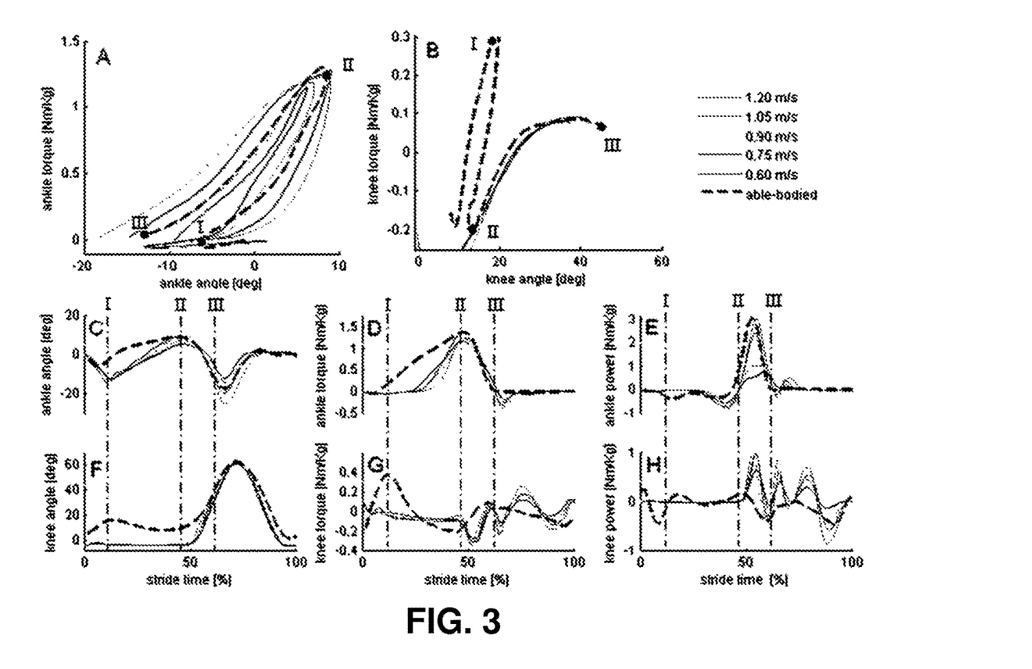
FIG. 3 displays graphs of ankle and knee joint kinetics and kinematics profiles.

FIG. 3 shows ankle and knee joint kinetics and kinematics profiles averaged over all the strides recorded at the same walking speed and normalized on stride duration. The graphs at FIG. 3 reflect mean prosthesis kinematics and kinetics profiles recorded at different walking speeds. Solid lines represent the profiles averaged among all strides completed at the same walking speed. Time is normalized by stride duration. Torque and power are divided by user's body weight.

Panels A, C, D, and E of FIG. 3 show quasi-stiffness, angle, torque, and power profiles for the ankle joint, respectively. Panels B, F, G, and H show the same variables, respectively, for the knee joint. Solid lines indicate the averaged profiles; shaded areas represent +/− one standard deviation. As a term of comparison, able-bodied data extracted from D. A. Winter, Biomechanics and Motor Control of Human Movement, vol. 2nd. 1990, p. 277, are shown by black dashed lines. Roman numerals I, II, and III indicate the averaged transition times from early to mid-stance, from mid- to late-stance, and from late-stance to swing phase, respectively.

A visual analysis of kinetics and kinematics highlights the ability of the proposed controller to approximate the biomechanical behavior of intact legs. The finite-state machine performed robustly, allowing the correct and timely identification of all gait-phase transitions. Transitions between different 2D-LUTs in stance phase, as well as the switch to position control in swing phase, were all very smooth, giving the user improved comfort and confidence while walking with the prosthesis.

During early stance, we observed the most significant difference between the prosthesis and the intact-leg quasi-stiffness and kinematics profiles. At the beginning of the gait cycle, the physiological knee trajectory (black shaded lines, FIG. 3F) shows a knee flexion movement, whereas the prosthetic knee joint remained locked on the mechanical endstop at −2°. Note that in FIG. 3B we omitted the knee torque when the mechanical stop was reached, as it was not possible to determine its contribution to the overall knee torque. The lack of stance knee flexion has previously been associated with the dynamics of body weight acceptance together with the compliance of the human thigh at the interface with the prosthesis socket. We believe this phenomenon was increased in our experiment by the higher compliance of the bypass adapter compared to a typical socket. Notably, the early stance knee hyperextension caused an exaggerated initial ankle plantarflexion movement (see panel C at FIG. 3), with a peak of about −12° at the transition between early and mid-stance. As a consequence, early stance lasted longer for the prosthesis than for the intact leg. As shown in panel A of FIG. 3, walking speed did not significantly affect the prosthesis behavior during early stance.

Prosthesis behavior in early stance clearly influenced the mid-stance progression. Knee hyperextension continued into mid-stance until the transition to late stance, at about 50% of the gait cycle, when the knee started flexing. Similarly, the exaggerated ankle plantarflexion angle in early stance produced a decreased dorsiflexion angle throughout mid-stance for all walking speeds. The prosthesis then recovered a physiological ankle angle towards the end of mid-stance. Interestingly, the maximum dorsiflexion angle recorded at the end of mid-stance (FIG. 3C and FIG. 4A) showed an increasing trend that progressively reached a plateau, in agreement with able-bodied data.

In agreement with other able-bodied studies, during mid-stance (FIG. 3A, from I to II), the ankle quasi-stiffness profile became progressively more non-linear as walking speed increased. The increased non-linearity reduced the initial breaking torque exerted by the ankle during this negative work phase of the gait-cycle (FIG. 3D), thus facilitating the inverted pendulum movement at increased walking speeds. As a result, ankle negative power in mid-stance (FIG. 3E) did not increase significantly with walking speed, despite the higher joint speed, as observed in intact leg studies.

During late stance (FIG. 3A, from II to III) the ankle quasi-stiffness profile shifted towards a more negative ankle angle as walking speed increased, mimicking intact ankle behavior. In turn, the shift of the quasi-stiffness profile increased the area described by the ankle torque-angle curve during overall stance phase (from I to III), resulting in greater mechanical work production (see FIG. 5A). Late stance is particularly critical for the efficiency and stability of walking. During late stance, able-bodied persons increase the positive energy provided through the ankle joint, in proportion to walking speed, in order to compensate for the greater energy dissipation caused by the impact of the foot with the ground at faster speeds. By enforcing intact-leg quasi-stiffness profiles based on walking speed, our controller achieved physiological ankle energetic behavior. Providing controlled positive energy during late stance with a powered ankle-foot prosthesis effectively reduced the metabolic cost of walking for people with transtibial amputations. This further motivated us to investigate our controller in transfemoral amputees.

It is worth noting that, at the transition between mid- to late stance, the intact-leg ankle torque exceeded the measured ankle torque. This was due to a limitation of the prosthesis hardware imposed by its ankle motor strength, and is therefore not related to our controller. On the other hand, the knee joint required lower torque than the ankle, allowing us to provide the quasi-stiffness profile without motor saturation (see in FIG. 3B).

Figure 4:
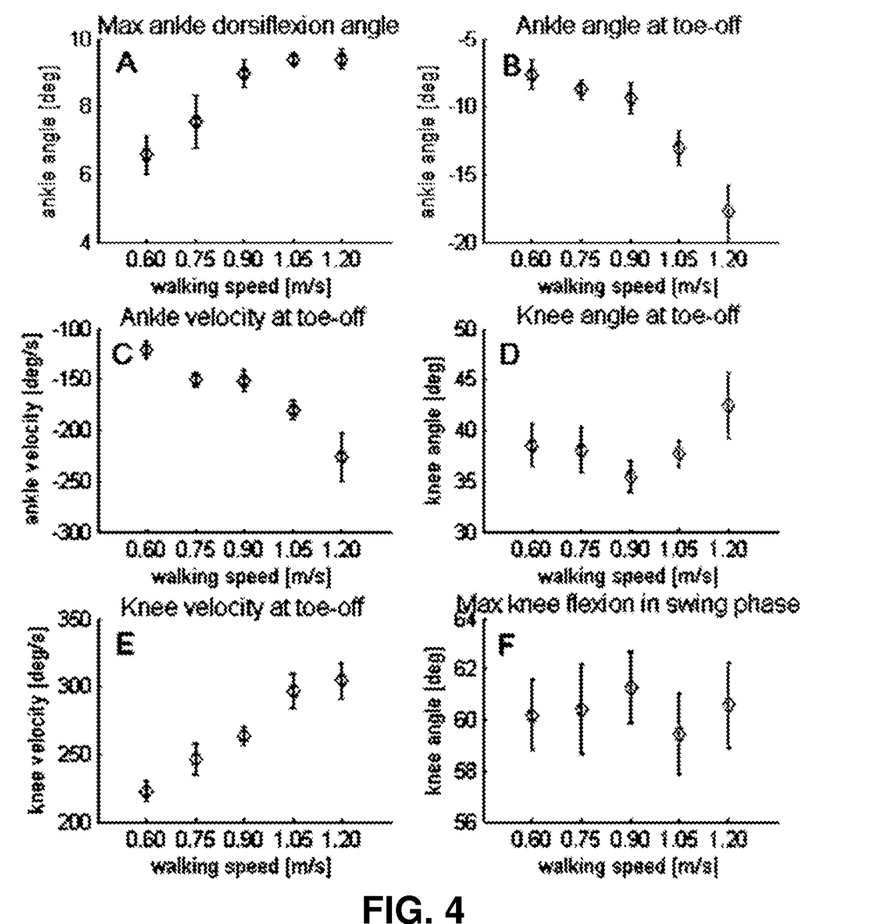
FIG. 4 displays graphs reflecting averaged kinematics parameters as a function of walking speed.

The quasi-stiffness modulation (from II to III) significantly affected joint kinematics and kinetics in late stance. Higher torque was provided for the same ankle angle at increasing walking speeds. This resulted in a greater plantarflexion angle during late stance. This trend is captured in FIG. 4, which displays graphs reflecting averaged kinematics parameters as a function of walking speed. FIG. 4A reflects maximum ankle dorsiflexion angle. FIGS. 4B and C show the ankle plantarflexion angle and velocity at toe-off as a function of walking speed. In contrast, the knee angle at toe-off (FIG. 4D) showed a u-shaped trend that cannot be directly connected with the adaptation of quasi-stiffness. FIG. 4E reflects knee velocity at toe-off and FIG. 4F reflects maximum knee flexion angle in swing phase.

Figure 5:
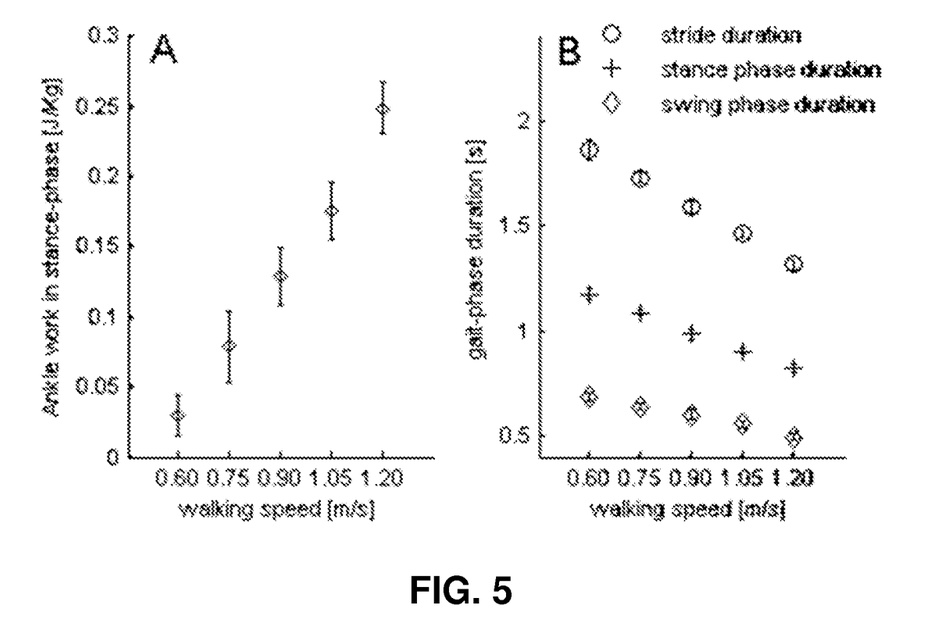
FIG. 5 displays graphs reflecting mechanical work and phase duration as a function of walking speed.

The swing trajectory generator approximated the able-bodied data for all tested walking speeds (FIGS. 3C and F). As walking speed increased, stance phase duration decreased (see cross markers in FIG. 5B). FIG. 5A is a graph reflecting mechanical work performed by the ankle joint during stance phase as a function of walking speed. FIG. 5B is a graph reflecting stride, stance phase, and swing phase duration as a function of walking speed. To maintain biologically appropriate swing timing across different walking speeds, the duration of the knee swing movement was modulated by the trajectory generator on a step-to-step basis to last 0.6 times the duration of the previous stance phase. As shown in FIG. 5B, this approach allowed maintenance of physiological stance and swing phase duration at all walking speeds. This was fundamental to ensure proper use of the robotic prosthesis, given that gait asymmetries have been shown to decrease the stability and energy efficiency of the gait.

Different walking speeds imposed very different conditions at the stance/swing phase transitions, as shown by the varying knee angles and velocities at toe-off in FIGS. 4D and E. Despite varying initial conditions, the swing trajectory generator consistently provided a biologically accurate trajectory (see FIG. 3F). Importantly, the maximum knee flexion angle during swing phase (FIG. 4F) was not altered by walking speed. This condition was fundamental to ensure the safety of the user when walking at varying speeds, as the knee maximum flexion angle in swing phase guarantees a proper foot clearance. As can be seen in FIGS. 3E and 3H, the joint torque was automatically adapted by the controller based on the speed of the swing movement. As expected from the dynamic model of the leg, torque increased proportionally to walking speed. The analysis of torque profiles at the transition between stance and swing phase also indicates that transitions between the two different controllers were very smooth. A smooth stance/swing transition is necessary to achieve comfort and increase the user's confidence while walking with the prosthesis.

Conclusions

We have designed and conducted preliminary testing of a new control framework for a robotic transfemoral prosthesis. Our controller relies on intact-leg quasi-stiffness in stance phase and a minimum jerk principle in swing phase. Using these two simple constraints allowed for biologically accurate behavior across different walking speeds, without user- or speed-specific tuning. Although the systems and methods described herein may be used in connection with a prosthesis, word "prosthesis" is used here, it should be understood that the controller we have described could be used in connection with other assistive devices, such as orthoses or exoskeletons.

What is claimed is:

1. A method for operating a joint of a prosthesis during a phase of stance, comprising:
   a. determining a joint angle of the joint;
   b. determining a walking speed magnitude of the prosthesis;
   c. retrieving, using only the joint angle and the walking speed, a torque value from an intact leg's quasi-stiffness profile,
   wherein the quasi-stiffness profile is representative of torque data for an able-bodied joint,
   wherein the able-bodied joint corresponds to the joint of the prosthesis, and
   wherein the intact leg's quasi-stiffness profile is encoded in a lookup table stored in a memory; and
   d. initiating a signal to apply a torque to the joint of the prosthesis in an amount based on the torque value.

2. The method of claim 1, further comprising operating the prosthesis on a ground; and determining an inclination of the ground at the position under the prosthesis; wherein the step of retrieving the torque value from the lookup table stored in the memory is based on the inclination of the ground.

3. The method of claim 1, wherein the method is used to control the prosthesis during an early phase of stance, a mid-phase of stance, and a late phase of stance.

4. The method of claim 1, wherein the joint of the prosthesis is the knee joint.

5. A method for operating a prosthesis comprising a knee joint and an ankle joint during a phase of stance, comprising performing the method of claim 1 for the knee joint and performing the method of claim 1 for the ankle joint.

6. The method of claim 1, where the torque value is retrieved from the lookup table using interpolation.

7. The method of claim 1, wherein the signal to apply the torque to the joint of the prosthesis is modified, based on a weight of the user of the prosthesis, to normalize the torque to apply.

8. The method of claim 1, wherein the method is used to control the prosthesis during an early phase of stance, a mid-phase of stance, and a late phase of stance.

9. The method of claim 1, wherein the joint of the prosthesis is the knee joint.

10. A method for operating a prosthesis comprising a knee joint and an ankle joint during a phase of stance, comprising performing the method of claim 1 for the knee joint and performing the method of claim 1 for the ankle joint.

11. The method of claim 1, where the torque value is retrieved from the lookup table using interpolation.

12. The method of claim 1, wherein the signal to apply the torque to the joint of the prosthesis is modified, based on a weight of the user of the prosthesis, to normalize the torque to apply.

13. The method of claim 1, wherein the lookup table is selected from a plurality of lookup tables.

14. The method of claim 13, wherein each lookup table in the plurality of lookup tables is associated with a distinct phase of stance.

15. The method of claim 1, wherein the determining the walking speed magnitude of the prosthesis comprises measuring a shank orientation of a user of the prosthesis using a complementary filter.

16. A method for operating a joint of a prosthesis, comprising:

a. setting the prosthesis to a first stance phase and, while the prosthesis is in the first stance phase:
determining a first joint angle of the joint;
determining a first walking speed of the prosthesis;
retrieving, using only the first joint angle and the first walking speed, a first torque value from a first intact leg's quasi-stiffness profile,
wherein the quasi-stiffness profile is representative of torque data for an able-bodied joint,
wherein the able-bodied joint corresponds to the joint of the prosthesis in the first stance, and,
wherein the intact leg's quasi-stiffness profile is encoded in a first lookup table stored in a memory; and
initiating a first signal to apply a torque to the joint of the prosthesis in an amount based on the first torque value; and b. setting the prosthesis to a second stance phase and, while the prosthesis is in the second stance phase:
determining a second joint angle of the joint;
determining a second walking speed of the prosthesis;
retrieving, using only the second joint angle and the second walking speed, a second torque value from a second intact leg's quasi-stiffness profile,
wherein the quasi-stiffness profile is representative of torque data for the able-bodied joint in the second stance,
and wherein the intact leg's quasi-stiffness profile is encoded in a second lookup table stored in a memory; and
initiating a second signal to apply a torque to the joint of the prosthesis in an amount based on the second torque value.

17. The method of claim 16, further comprising smoothing the second signal after a transition from the first stance phase to the second stance phase.

18. The method of claim 17, wherein the smoothing occurs during the 20 ms following the transition.

19. The method of claim 16, wherein step (b) occurs when a movement of an ankle joint of the prosthesis inverts between dorsiflexion and plantarflexion.

* * * * *